(12) United States Patent
Guehring et al.

(10) Patent No.: US 7,966,055 B2
(45) Date of Patent: Jun. 21, 2011

(54) MAGNETIC RESONANCE SYSTEM AND METHOD FOR CARDIAC IMAGING

(75) Inventors: Jens Guehring, Monmouth Junction, NJ (US); Michaela Schmidt, Buckenhof (DE); Peter Speier, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 893 days.

(21) Appl. No.: 11/756,802

(22) Filed: Jun. 1, 2007

(65) Prior Publication Data

US 2008/0009709 A1 Jan. 10, 2008

(30) Foreign Application Priority Data

Jun. 2, 2006 (DE) .................... 10 2006 025 915

(51) Int. Cl.
*A61B 5/055* (2006.01)

(52) U.S. Cl. ....................... 600/411; 600/416

(58) Field of Classification Search .................... 600/411
See application file for complete search history.

(56) References Cited

U.S. PATENT DOCUMENTS

| 6,792,066 B1 | 9/2004 | Harder et al. |
| 7,227,358 B2 | 6/2007 | Lehtonen-Krause |
| 7,711,160 B2 | 5/2010 | O'Donnell et al. |
| 2005/0075567 A1* | 4/2005 | Skyba et al. ................ 600/443 |
| 2006/0241379 A1 | 10/2006 | Greiser et al. |

* cited by examiner

*Primary Examiner* — Brian Casler
*Assistant Examiner* — Jonathan G Cwern
(74) *Attorney, Agent, or Firm* — Schiff Hardin LLP

(57) ABSTRACT

In a method for representation of the heart in a magnetic resonance system at least one MR overview image of the heart is acquired. An image plane with a predetermined position relative to the magnetic resonance system is selected for this overview image. The acquired MR overview image is displayed and a number of marking points are established in the displayed overview image. Further image planes for representation of the heart are calculated using some of the established marking points. Further MR images are acquired in the calculated image planes.

12 Claims, 6 Drawing Sheets

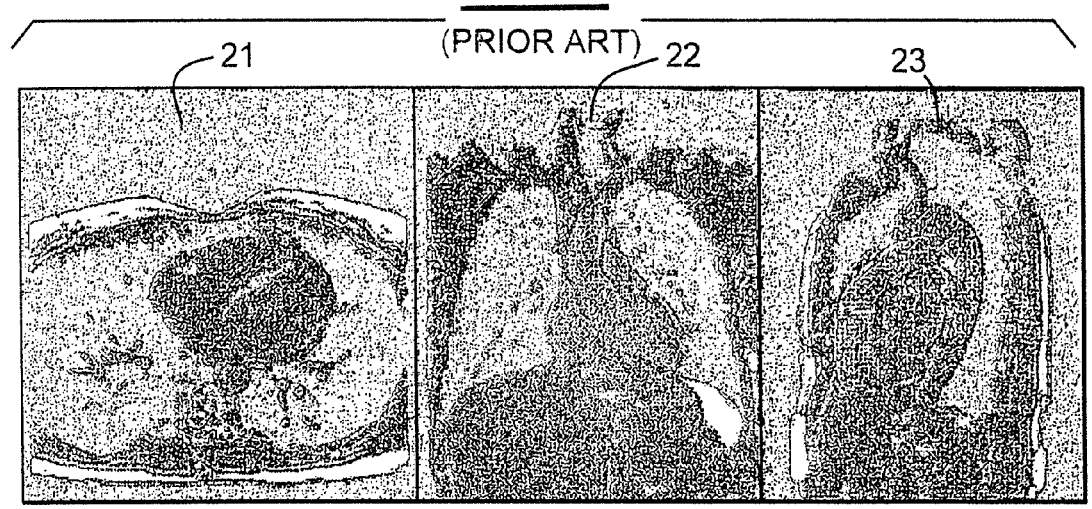
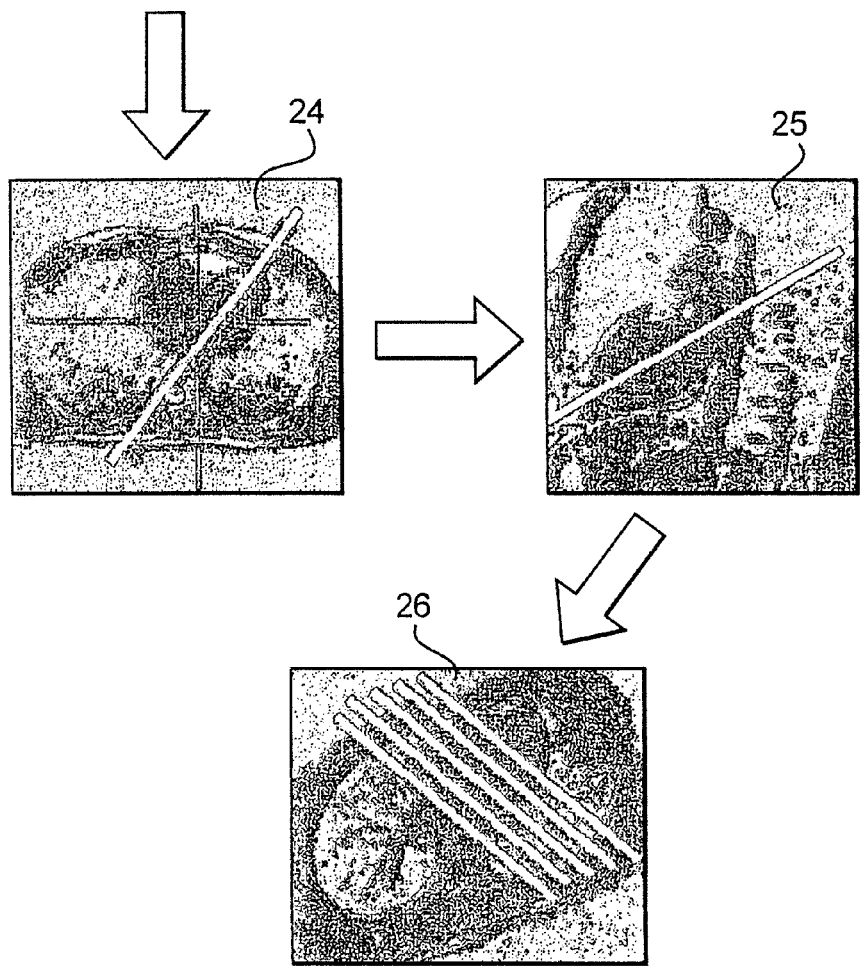
FIG. 2
(PRIOR ART)

MAGNETIC RESONANCE SYSTEM AND METHOD FOR CARDIAC IMAGING

BACKGROUND OF THE INVENTION

1. Field of the Invention

The present invention concerns a method for imaging of the heart by means of magnetic resonance, as well as a magnetic resonance system for this purpose.

2. Description of the Prior Art

Coronary heart diseases are the most frequent cause of death in the industrial nations, such that diagnosis of heart diseases plays an important role. For this reason it is important to obtain a precise representation of the anatomy and the functioning of the heart. For example, among other things questions such as "Do the coronary arteries exhibit stenoses?", "Does the perfusion of the heart at rest and under stress suffice to supply the myocardium?", "How significantly does the wall thickness increase in systole?" (known as the function reserve) or "How does the vitality of the heart muscle behave, for example after an infarct?" must be answered with the heart imaging. Among other things, coronary angiography, nuclear medicine, computed tomography as well as magnetic resonance tomography are available to answer such questions. Through the development of newer imaging sequences it has become possible in magnetic resonance tomography to acquire images of the heart with the necessary temporal resolution.

In examinations of the heart with magnetic resonance systems, the image plane can be freely selected in addition to the coronary, sagittal or transversal slice planes. For diagnostically significant exposures of the heart, however, images are needed that are acquired along the coordinate axes of the heart, i.e. along the long axis of the heart and along the short axis of the heart. The localization of the primary orientation of the heart in MR imaging is protracted and requires medically-trained personnel. For this reason such an examination can be conducted only by trained medical personnel. The inhibition (reluctance) threshold (in particular for operating personnel who are not health professionals) to conduct heart examinations is therefore very large. Furthermore, even for trained personnel heart examinations are very complicated since various steps are necessary in order to find the ideal image planes.

An exemplary sequence of steps that must be implemented to allow MR images to be generated along the coordinate axes of the heart is shown in FIG. 2. Conventionally the heart is for the most part localized in four steps, with each step building on the image acquired in the preceding step. Typical overview images 21, 22 and 23 are first acquired: an overview image in the transversal slice 21, one overview image in the coronary slice 22 and one overview image in the sagittal slice 23. The image plane of the long heart axis then can be planned parallel to the septum on the transversal slice through the left ventricle, as is shown in image 24. An image of the heart as shown in image 25 results in the image plane that was planned in image 24. In this image 25, the horizontal long axis can be planned through the apex of the heart and the middle of the mitral valve. The image 26 results with the image plane that was planned in image 25. With image 26, 6-10 image planes are typically planned along the short axis parallel to the valves and perpendicular to the heart septum. After this, the three image planes must be planned with these images along the long axis (known as the two-chamber view, the three-chamber view and the four-chamber view). Images with the image plane along specific axes (called short axes) orthogonal to the long axis must be planned with these images of the long axis.

As is apparent from the above description, the localization of the heart is time-consuming and requires medically-trained operating personnel.

SUMMARY OF THE INVENTION

An object of the present invention is to provide a method for representation of the heart by means of magnetic resonance tomography, which can be implemented by less-trained personnel and that is less time-consuming (and therefore more cost-efficient).

This object is achieved in accordance with the invention by a method for representation of the heart in a magnetic resonance system, wherein at least one MR overview image of the heart is acquired in a first step, whereby an image plane with a predetermined position relative to the magnetic resonance system being selected for this overview image. An MR overview image is subsequently acquired in this one predetermined image plane, this MR overview image being subsequently shown on the MR system display for the operating personnel. A number of marking points then can be established on the displayed overview image that was acquired in a predetermined position. After the marking points have been established, further image planes for representation of the heart are automatically calculated using some of the established marking points. Further MR images of the heart are subsequently acquired in the calculated image planes. The method according to the present invention has the advantage that further overview images in various positions no longer have to be acquired, as described in connection with FIG. 2. It is only still necessary to acquire a first overview exposure in a specific, established position. Studies have shown that there is a specific orientation of the image plane relative to the patient in which MR images of the heart can be generated that can then subsequently be used (by establishment of a few marking points) in order to automatically determine the other image planes. The heart orientation and position do in fact vary from patient to patient, but so little that this same slice orientation can be selected independently of the patient.

According to the invention, if this predetermined position of the image plane is the same for all examined persons, it is the pseudo-short axis slice of the heart. A slice stack in this orientation is acquired in which the right ventricle and the left ventricle as well as both atria and the large vessels of the heart are recognizable.

This predetermined image plane can advantageously be achieved by moving a specific region of the body into the center of the basic field magnet of the magnetic resonance examination system. After a precise positioning of the examination person in the center of the magnet, the image plane is then automatically established with a predetermined angle and in a predetermined position relative to this magnetic center. The position of this image plane, for example, can be stored as a preset in the magnetic resonance system, so that the operating personnel must only call up this position of the image plane in order to generate the overview image. Naturally, as is typical, it is furthermore possible to generate additional transversal, coronary and sagittal overview images of the body in the event that these are required during the further examination. These transversal, sagittal or coronary overview images, however, are no longer absolutely necessary.

According to a further embodiment of the invention, marking points are then established on the MR image that was acquired in the image plane of the pseudo-short axis slice. For example, some or all of the following points can be marked on the images: the heart base of the left ventricle, the apex of the heart, the base of the right ventricle, the left atrium and/or the aorta as well as points on the intersection of right ventricle and left ventricle. The image planes of the long heart axes then can be calculated automatically from these marking points. For example, the position of the image plane for the two-chamber view can be determined with the marking points "base of the left ventricle", "apex", and the orientation of this two-chamber view can be determined from the connecting line of the intersection points from the right ventricle and left ventricle. The orientation of the two-chamber view, however, is advantageously selected orthogonal to a vector that arises by averaging two connection vectors A and B, with A=left ventricle to base of right ventricle and B=left ventricle to aorta. The left ventricle and the left atrium are shown truncated in the two-chamber view.

Furthermore, it is possible to determine the image plane for the three-chamber view with the aid of the marking points "aorta", "apex" and "left atrium". The image plane for the four-chamber view (right and left ventricles, right and left atria) can be determined, for example, using the marking points "base of left ventricle", "apex", "base of right ventricle".

Image planes for images along the short heart axis then can be automatically calculated from the calculated image planes of the long axes, these image planes lying essentially perpendicular to the long axes from the heart base to the heart apex.

The marking points described above furthermore can be used for a segmentation of the heart muscle for quantitative analysis of the function of the left ventricle. It is likewise possible to generate a heart model by determination of two further points (intersection of right ventricle and left ventricle).

The marking points advantageously can also be used to improve automatic segmentation algorithms. For example, the myocardium is segmented in many applications. If the position of some of these marking points is now known, a segmentation algorithm can be improved when some of these marked anatomical points are established. It is also possible to automatically implement segmentation algorithms on the images of the pseudo-short axis slice and then to calculate and to display markings as start values for the individual marking points, based on the results of the automatic segmentation. The final determination of the marking points thus is made simpler for operating personnel.

DESCRIPTION OF THE DRAWINGS

FIG. 2 shows steps for heart imaging according to the prior art.

DESCRIPTION OF THE PREFERRED EMBODIMENTS

Figure 1:
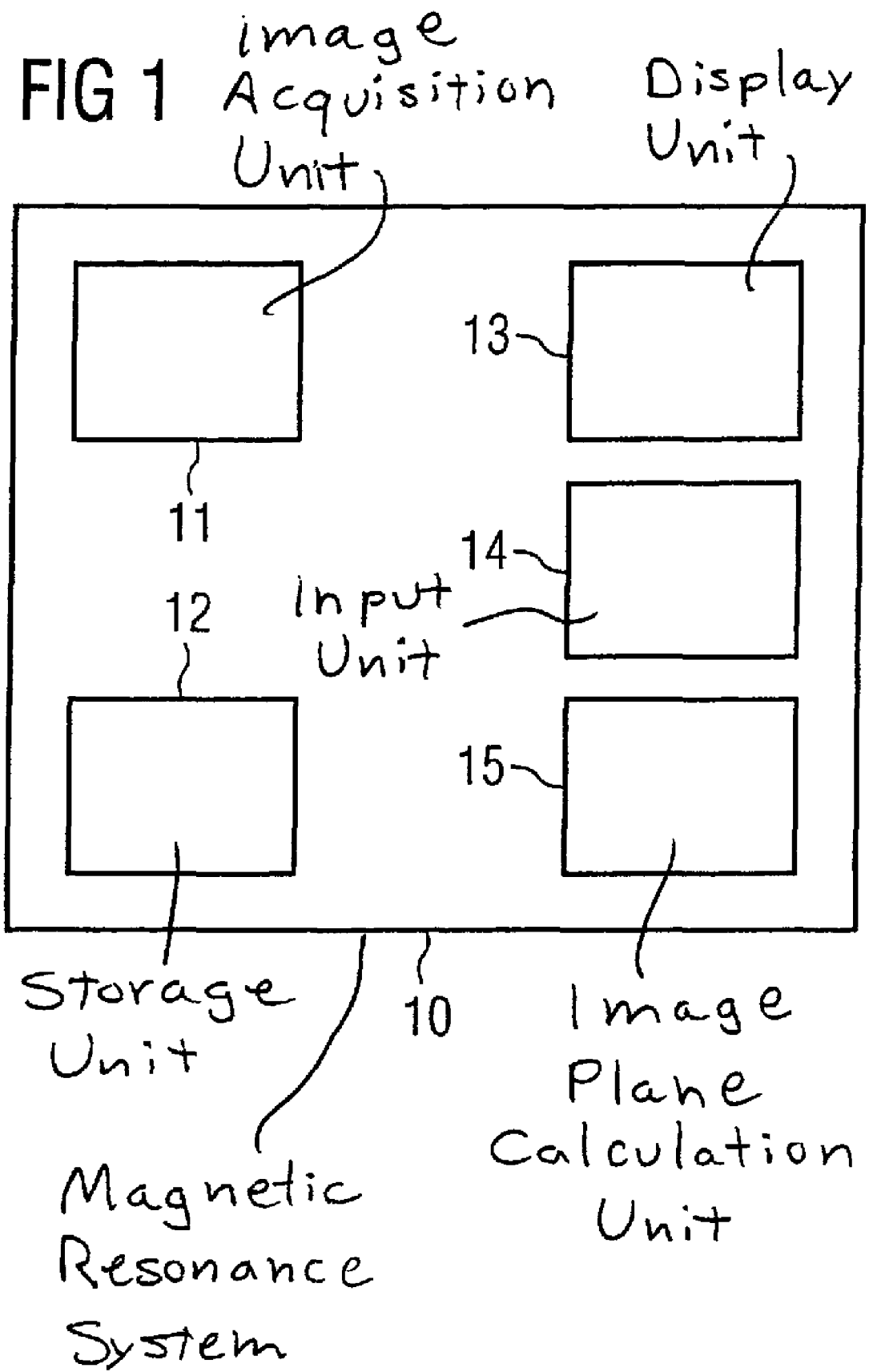
FIG. 1 schematically shows the basic compounds of a magnetic resonance system according to the invention.

FIG. 1 schematically shows a magnetic resonance (MR) system 10. The basic design and the interaction of the various components of a magnetic resonance system (such as, for example, basic field magnet, gradient coils, RF irradiation with radio-frequency antenna, reception antenna etc.) are known to those skilled in the art and need not be described further herein since they are not of importance for the understanding of the invention. Only the components that are necessary for the understanding of the invention are described here. The schematic magnetic resonance system 10 shown in FIG. 1 includes an image acquisition unit 11 for acquisition of the MR images, in particular here the overview image. Naturally the other MR images are also acquired with the image acquisition unit 11. Furthermore, a storage unit 12 is provided in which at least the predetermined orientation and position of the image plane relative to the middle of the magnet of the resonance system is stored. The MR images acquired with the image acquisition unit 11 are presented on a display unit 13. Furthermore, an input unit 14 is provided with which operating personnel can determine various marking points on the shown MR images. Furthermore, an image plane calculation unit 15 is provided that calculates further image planes for acquisition of MR images of the heart from marking points marked by the operating personnel.

Figure 3:
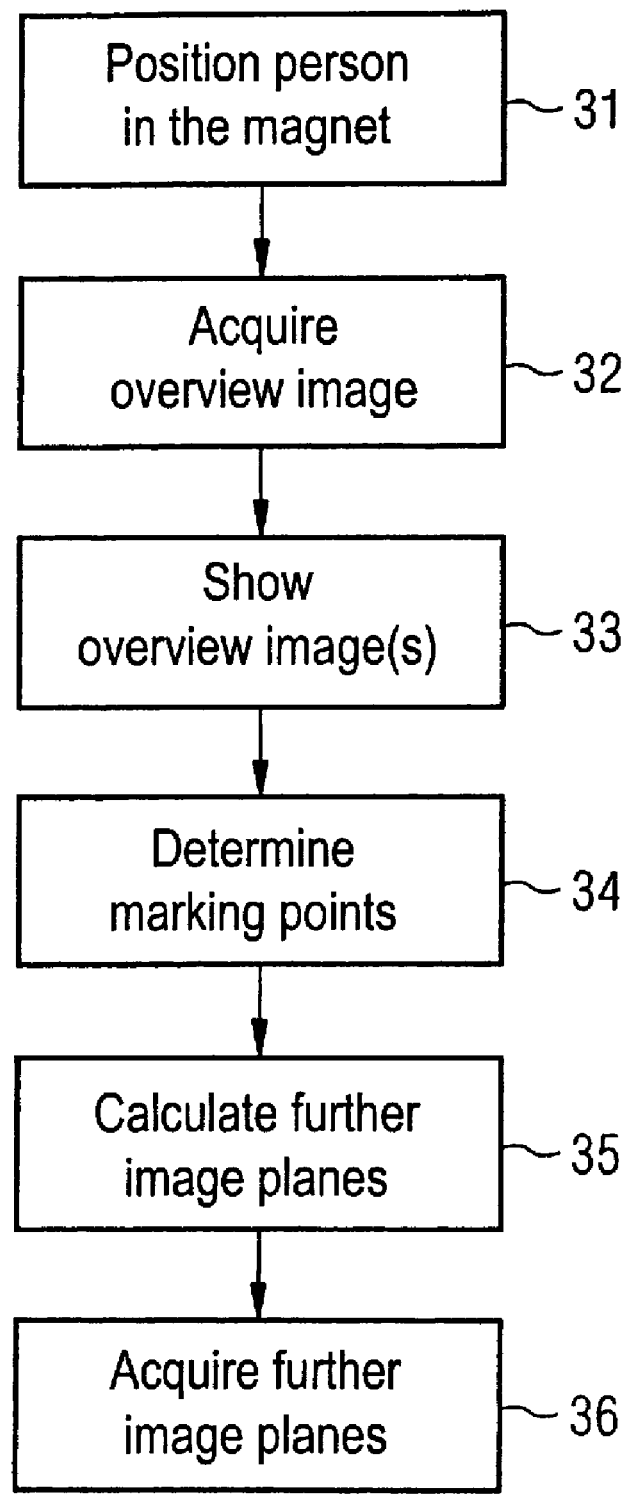
FIG. 3 is a flow chart of steps of an embodiment for presentation of the heart in accordance with the invention.
Figure 4:
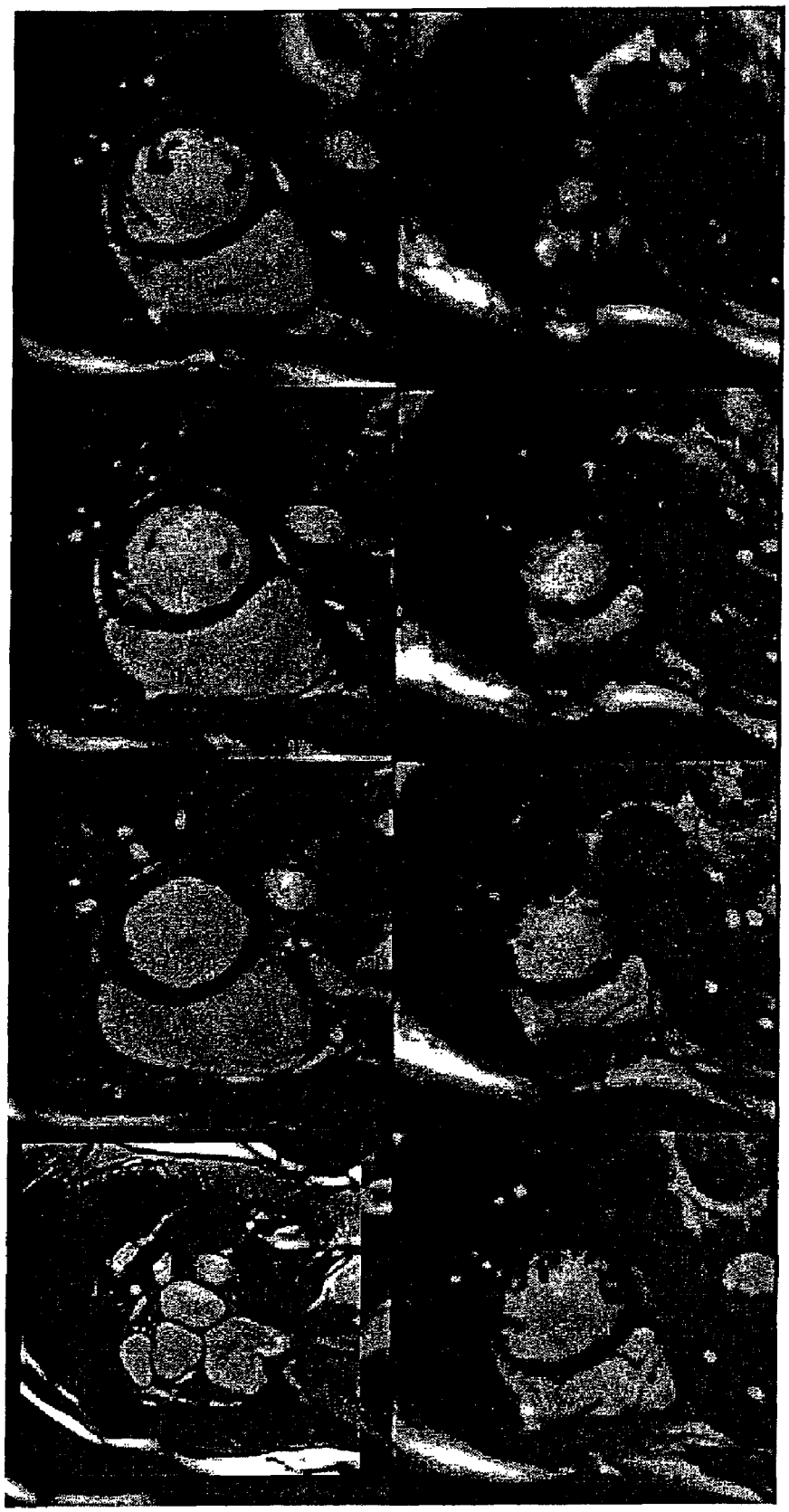
FIG. 4 shows exemplary images in a pseudo-short axis slice in accordance with the invention.
Figure 5:
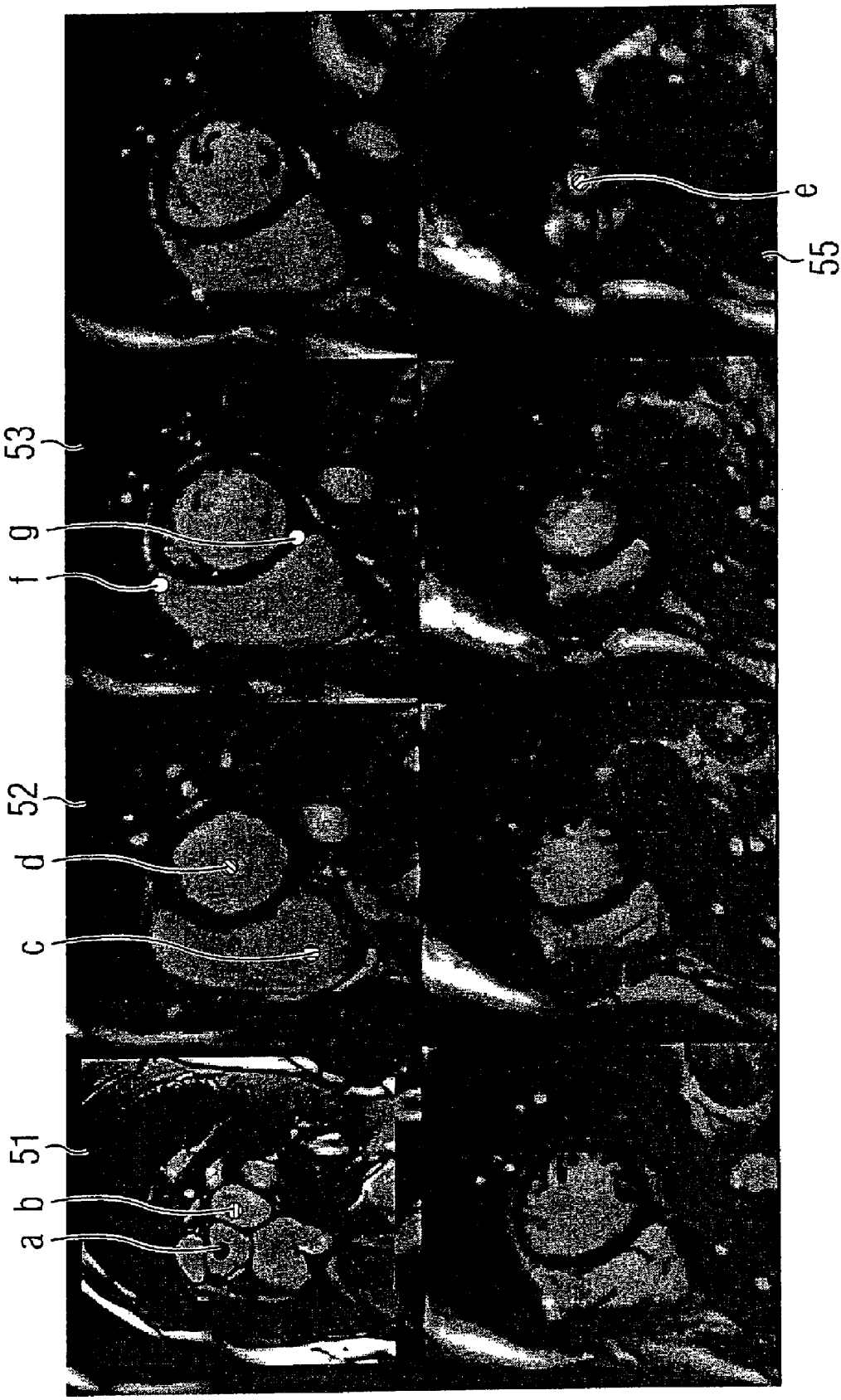
FIG. 5 shows an example of marking of the marking points for calculation of the further image planes in accordance with the invention.
Figure 6:
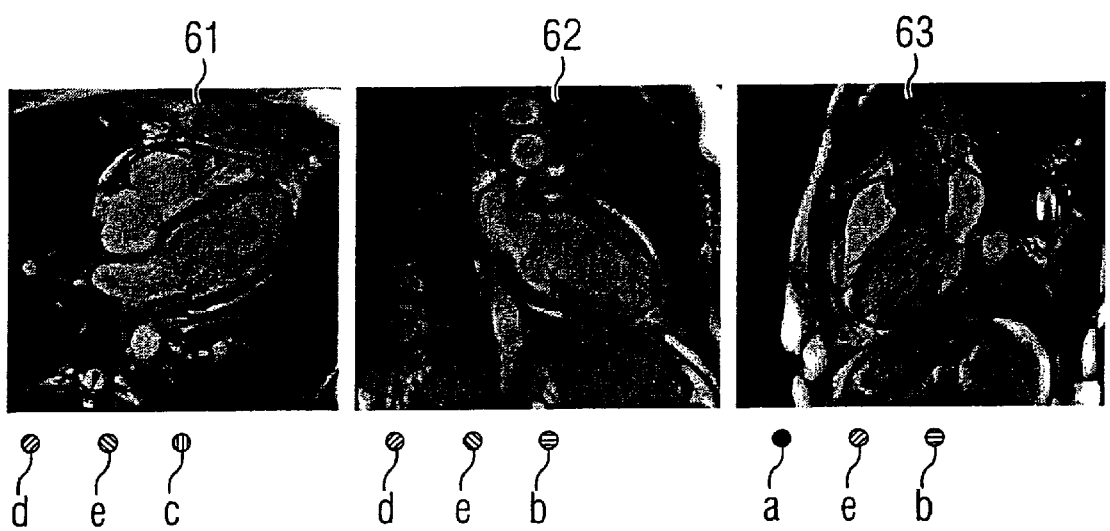
FIG. 6 shows various heart images along the long axis that was calculated with the different marking points in accordance with the invention.

The sub-steps that are necessary in order to generate MR images of the heart according to the invention are shown in a flow chart. In a first step 31 the examined person is centered precisely in the magnet, namely such that the heart lies in the center of the magnet. For this purpose, the lower end of the sternum is positioned in the magnet center. When the image plane for the overview image is established relative to the magnet, it must be taken into account that this applies only for one orientation of the examination person in the magnet. In heart acquisitions, the examination person typically is placed lying head first on his or her back in the magnet. If the examined person should be moved into the magnet feet-first, the predetermined position must naturally be correspondingly changed. In a step 32 an overview image is subsequently acquired with the aid of the image plane stored in the memory 12, thus the overview image is of the type known as a pseudo-short axis slice. This MR image acquired in the pseudo-short axis slice or the MR images acquired in the pseudo-short axis slice is/are shown on the display unit 13 in step 33. In step 34, as is described in connection with FIG. 5, the operating personnel can then mark a plurality of specific anatomical points in the images. As shown in image 51 in FIG. 5, for example, the aortic root a and the left atrium b can be marked in the pseudo-short axis slice. As shown in image 52, the base of the right ventricle c and the base of the left ventricle d can likewise be marked. As shown in image 55, the apex e can likewise be marked. The various positions of the long axis can then be calculated from these marked points a-e, as is shown in FIG. 6. For example, as shown in image 61 the image plane of the four-chamber view can be calculated with the marking points d, e and c, i.e. the base of the left ventricle, apex and the base of the right ventricle. As shown in image 62, the position of the two chamber view can be calculated with the marking points "base of left ventricle" d) and "apex" e) and the left atrium b) and the orientation of the two-chamber view can be calculated with the intersection points f) and g). The image plane for the three-chamber view that is shown in image 63 can be calculated with the aid of the marking points aortic root a), cardiac apex e) and left atrium b). Referring again to FIG. 3, the calculation of the further image planes is shown in step 35. When the further image planes with the marking points a-e have been calculated, in step 36 acquisitions are subsequently, automatically made in these image planes. After the image planes for the long axes that lead to the images 61-63 (cannot be shown) have been calculated, image planes for the short axes perpendicular to the long axes are calculated from the heart base to the cardiac apex.

In a further embodiment (for example as shown in image 53) the slice points f and g from the right ventricle and from the left ventricle are marked. Finally, a generation of a heart model is possible with these further points.

In summary, the present invention enables a simpler and faster localization of the heart, whereby the long and short heart axes are automatically located after input of anatomical markings that are simple to find. A heart examination by means of magnetic resonance tomography can also be conducted by less-trained personnel through this automatic calculation of the image planes. Furthermore, a distinct time savings results relative to the previously-used method as it was described in FIG. 2. The heart imaging by means of magnetic resonance can be introduced into the clinical routine with the method described above.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for representing a heart of a subject by magnetic resonance (MR), using an MR system, comprising the steps of:
   acquiring at least one MR overview image of a heart in an image plane having a predetermined position relative to the MR system;
   visually displaying the acquired MR overview image;
   allowing user interaction with the displayed MR overview image to manually mark five punctiform marking points at respective anatomical points in the displayed MR overview image;
   automatically electronically calculating three image planes each containing the long axis of the heart using only the five manually marked marking points; and
   acquiring further MR images respectively in the calculated three image planes.

2. A method as claimed in claim 1 comprising selecting said predetermined position of the image plane of the MR overview image as the pseudo-short axis slice, which contains the right and left ventricles, both atria, and the large vessels of the heart.

3. A method as claimed in claim 1 comprising establishing said five manually marked marking points on the displayed MR overview image by manually marking at least two points on a straight line defined by the base of the left ventricle and the apex of the heart.

4. A method as claimed in claim 1 comprising automatically electronically calculating image planes for respective images of the short axis of the heart from the image planes for the long axis of the heart, as planes that are substantially perpendicular to the long axis of the heart.

5. A method as claimed in claim 1 wherein said MR system comprises a magnet having a center, and comprising moving the subject to cause a predetermined region of the body of the subject to be located at the center of the magnet for acquiring said MR overview image, with said MR overview image being in an image plane having a predetermined angle and a predetermined position relative to said center of said magnet.

6. A method as claimed in claim 1 comprising marking additional manually marked marking points in the displayed overview image respectively designating intersection points of the right ventricle and the left ventricle, and automatically electronically generating a heart model from said five manually marked marking points and the manually marked intersection points.

7. A method as claimed in claim 1 comprising automatically electronically determining a quantitative function of the left ventricle of the heart using said five manually marked marking points on the displayed overview image.

8. A method as claimed in claim 1 comprising automatically electronically segmenting respective anatomical regions of the heart using said five manually marked marking points on the displayed overview MR image.

9. A method as claimed in claim 1 comprising automatically electronically segmenting images of the pseudo-short axis slice, which contains the right and left ventricles, both atria, and the large vessels of the heart, using said five manually marked marking points on the displayed overview MR image.

10. A method as claimed in claim 1 comprising selecting said predetermined position of the image plane of the MR overview image as the pseudo-short axis slice, and automatically electronically segmenting anatomical regions of the heart implemented on images of the pseudo-short axis slice, which contains the right and left ventricles, both atria, and the large vessels of the heart, and automatically electronically calculating starting marking points for the automatic segmentation and displaying the automatically calculated starting marking points.

11. A method as claimed in claim 1 comprising marking, as said five manually marked marking points, respective points designating the left ventricle of the heart, the apex of the heart, the aorta, the left atrium of the heart, and the base of the right ventricle of the heart, and automatically electronically calculating, from the respective points designating the left ventricle of the heart and the apex of the heart, a first of said three image planes for a two-chamber view of the heart, and automatically calculating, from the respective points designating the aorta, the apex of the heart and the left atrium of the heart, a second of said three image planes for a three-chamber view of the heart, and automatically electronically calculating, from the respective points designating the left ventricle of the heart, the apex of the heart, and the base of the right ventricle of the heart, a third of said three planes for a four-chamber view of the heart.

12. A magnetic resonance (MR) system for representing a heart of an examination subject, said MR system comprising:
   an image acquisition unit that interacts with a subject therein to acquire MR data therefrom;
   a memory unit having stored therein a predetermined image plane with a predetermined orientation and angle relative to the image acquisition unit;
   a control unit, having access to said memory unit, that operates said image acquisition unit to acquire MR data from a subject representing at least one MR overview image of the heart of the subject in said predetermined image plane;
   a display unit that displays the acquired MR overview image;
   an input unit allowing manual marking of five punctiform marking points at respective anatomical points on the MR overview image displayed at the display unit; and
   an image plane calculation unit that automatically calculates three image planes each containing the long axis of the heart of the subject from only the five manually marked marking points on the displayed MR overview image, said control unit controlling said image acquisition unit to acquire further MR images of the heart of the subject respectively in the calculated three image planes.

* * * * *